United States Patent [19]

Rudnick et al.

[11] Patent Number: 5,395,538
[45] Date of Patent: Mar. 7, 1995

[54] ALKYLATED THIOPHENE LUBRICANTS

[75] Inventors: Leslie R. Rudnick, Lawrenceville; Carleton N. Rowe, Wenonah, both of N.J.

[73] Assignee: Mobil Oil Corporation, Fairfax, Va.

[21] Appl. No.: 190,712

[22] Filed: Jan. 28, 1994

Related U.S. Application Data

[63] Continuation of Ser. No. 961,309, Oct. 15, 1992, abandoned, which is a continuation-in-part of Ser. No. 752,137, Aug. 29, 1991, abandoned.

[51] Int. Cl.$^6$ .............. C10M 134/34; C10M 105/72; C07D 333/08
[52] U.S. Cl. .......................................... 252/45; 549/86
[58] Field of Search ............................. 252/45; 549/86

[56] References Cited

U.S. PATENT DOCUMENTS

| | | | |
|---|---|---|---|
| 2,160,293 | 5/1939 | Shoemaker | 252/45 |
| 2,328,782 | 11/1950 | Reiff | 252/45 |
| 2,417,087 | 3/1947 | Prutton | 252/42.7 |
| 2,448,211 | 8/1948 | Caesar et al. | 260/329 |
| 2,480,832 | 9/1949 | Brooks et al. | 252/45 |
| 2,552,769 | 5/1951 | Caesar | 260/329 |
| 3,395,101 | 7/1968 | Clark | 252/48.8 |
| 5,171,915 | 12/1992 | Forbus et al. | 585/455 |

OTHER PUBLICATIONS

Hackh's Chemical Dictionary, Fourth Edition, p. 677 "thiophen(e)", 1972 (month unknown).

*Primary Examiner*—Jerry D. Johnson
*Attorney, Agent, or Firm*—A. J. McKillop; M. D. Keen

[57] ABSTRACT

Alkylated thiophene compounds are high temperature stable lubricant fluids having excellent thermal stability, antiwear and load-carrying properties and excellent additive solubility.

7 Claims, No Drawings

ALKYLATED THIOPHENE LUBRICANTS

This a continuation of application Ser. No. 07/961,309, filed on Oct. 15, 1992, now abandoned, which is continuation-in-part of Ser. No. 752,137, filed Aug. 29, 1991, now abandoned.

BACKGROUND OF THE INVENTION

This invention is directed to improved lubricant and fuel compositions comprising alkylated thiophene lubricant fluids alone or in combination with synthetic or mineral oils, and to mineral or synthetic lubricant oil or hydrocarbyl or hydrocarbloxy fuel compositions containing minor amounts of said alkylated thiophenes as multifunctional additives therefor.

Polyphenyl sulfides and polyphenyl thioethers are known and have been used as lubricants/additives in special applications. Polyphenyl sulfides suffer from very high cost due to difficult synthesis and have poor low-temperature properties. Polyphenyl ethers are known for their high temperature properties as noted in D. Klamen's "Lubricants and Related Products" Verlag Chemie, 1984, pp. 116–121, and references contained therein, and also in, for example, the product bulletin for the commercial polyphenyl ether, OS-124 by Monsanto.

G.B. 1,093,945 to Neale is directed to the alkylation of diphenyl sulfides in the presence of aluminum chloride catalysts.

Incorporation of linear alkyl groups into diphenyl sulfide eliminates both of the above problems and provides a novel, relatively inexpensive lubricant having excellent low-temperature properties. The use of these adducts as a lubricant or lubricant additive in either mineral or synthetic lubricant has been recently disclosed (PD 90-145, L. R. Rudnick).

The principal limitation of getting monoalkylated fluids of diphenyl sulfide using lower olefins is obtaining high viscosity index. Alkylation of thiophene with hexadecene provides a monoalkylated adduct having a viscosity of 2.8 cSt and a VI of >125. This opens a wider range of application areas for alkyl aromatic sulfur-containing lubricating fluids.

Many alkylation processes are known in the art and the alkylation methods of much of the prior art are primarily directed to polysubstituted or polyalkylated products. See, for example, JA 5557391 to Matsumura which discloses the dialkylation of diphenyl ethers over aluminum chloride. U.S. Pat. No. 4,395,372 to Klutz discloses the alkylation of benzene over a zeolite to obtain a predominantly polyalkylated product unless the alkylation takes place in the presence of sulfur dioxide. On the other hand U.S. Pat. No. 4,664,829 to Arakawa alkylates a mixture of materials to obtain both mono- and polysubstituted material. Arakawa uses Friedel-Crafts type catalysts. Garces, U.S. Pat. No. 4,891,448 discloses the alkylation of polycyclic aromatics over natural zeolites such as mordenite, offretite and gmelinite.

Clark, U.S. Pat. No. 3,395,101, is directed to the use of tertiary alkyl thiophenols as lubricants and hydraulic fluids. However, these fluids comprise mixtures of mono- and dialkylthiophenes.

Shoemaker, et al. is directed to lubricants and to lubricant additives. The active material in the fluids of Shoemaker et al. appear to be compounds having one or more nitrogen groups in heterocyclic ring structures such as azoles and azines. The thiophenes disclosed are useful as additives for corrosion inhibition, etc.

We now disclose the preparation and use of monoalkylated thiophenes as a new class of lubricating fluids. These fluids have the advantages of alkylated diphenyl sulfides in that the polar sulfur provides excellent additive solubility and good lubricating properties. To the best of applicant's knowledge and belief, the herein described alkylated compounds have not been used previously as lubricants or additives.

BRIEF SUMMARY OF THE INVENTION

This application is directed to novel lubricant compositions comprising from about less than one percent to about 100% of alkylated thiophenes as disclosed herein and to mineral and synthetic lubricants and fuels containing minor proportions of the disclosed thiophenes as multifunctional additives.

The products obtained from the reaction of a linear olefin and thiophene in the presence of specific zeolite catalysts are unique not only in composition and structure but in utility. Part of the uniqueness is derived from the specific reaction over zeolite catalysts; generally, they have a higher VI at a given viscosity. The incorporation of various alkyl groups into the thiophene structure provides compositions of different viscosity and low temperature viscometrics. Synthesized catalysts are preferred to provide the improved high temperature stable products.

The thermal stability of these alkylated thiophenes is excellent and believed to be improved over materials of branched structure due to the facility for carbon-carbon bond breaking in the latter materials.

The use of these adducts as a lubricant or lubricant additive in either mineral or synthetic lubricants or as solid (group) lubricants or in solid lubricant compositions such as polyurea, lithium carboxylate or clay-thickened greases, is unique and provides improved properties and performance benefits due to inherent synergism. It is expected that the performance benefits will include antifatigue, antispalling, antistaining, antisquawking, improved additive solubility, improved load carrying/bearing, extreme pressure, improved thermal and oxidative stability, friction reducing, antiwear, anti-corrosion, cleanliness improving, low- and high-temperature antioxidant, demulsifying, emulsifying and detergency properties.

The products obtained from the alkylation of a linear olefin and a thiophene is a high temperature stable monoalkylation approaches 100% monoalkylated fluid.

Broadly, the novel class of hydrocarbon products of the present invention can be characterized as hydrocarbyl adducts of thiophenes. These hydrocarbon compositions may also be used in combination with additives, for example, antioxidants, EP/antiwear agents, inhibitors, detergents and dispersants, and viscosity index improvers. Non-limiting examples of antioxidants include phenols which can be hindered and aromatic amines. Non-limiting examples of EP/antiwear additives include zinc phosphorodithioates, sulfurized esters, sulfurized olefins, phosphonates, phosphites, phosphorothionates, etc. Non-limiting examples of inhibitors include DMTD, phenothiazine, etc. Non-limiting examples of detergents and dispersants include sulfonates, phenates, and polymeric succinimides. These can be either metallic or non-metallic. Metallic detergents can be calcium or magnesium derived and can be neutral or over based.

It is therefore an object of this invention to provide improved compositions comprising novel alkylated thiophene lubricant compositions in accordance with the invention and novel lubricant and fuel compositions containing minor proportions of said thiophenes as additives.

DESCRIPTION OF THE PREFERRED EMBODIMENTS

These unique lubricants exhibit beneficial properties from the unique reaction of olefin with the thiophene structure in such a way as to remain predominantly linear. This is a direct result of the catalytic reaction. This combination provides for the novel structural class disclosed here. The use of these compositions of matter as either functionalized alkyl/thiophene lubricant fluids or lubricant additives is believed to be novel.

More particularly, the novel class of hydrocarbon products of the present invention can be characterized as adducts of a hydrocarbyl substituent, which can contain one or more olefin groups, and a thiophene. The hydrocarbyl group can contain from $C_3$-$C_{500}$, preferably $C_6$-$C_{50}$ and most preferably $C_8$-$C_{18}$. The hydrocarbyl group can optionally contain S, N, O, P and/or F. The hydrocarbyl moiety can be alkyl, alkenyl, alkynyl, arylalkyl, aliphatic, cyclic, linear or branched. Substitution can be on one or more positions of the aromatic rings, with alkylation on either or both rings.

The preparation of these novel compositions is specifically by means of a zeolite catalytic addition reaction. The exact mechanism of the reaction is not important to the purposes of this invention, so long as the hydrocarbyl group becomes attached to the thiophene described herein.

One preferred method of reaction between the hydrocarbyl group and the thiophene is the combination of these reactants in the presence of specific zeolite catalysts. The zeolite catalysts should be at least partly in the acidic (H) form to provide the acidity for the reaction. The zeolites may contain other cations also, such as ammonium ($NH_4+$). The zeolite is preferably a large pore zeolite such as the faujasites, e.g., zeolites X, Y, USY, UHP-Y, ZSM-20 or zeolite beta. Another zeolite which may be used is zeolite MCM-22. Zeolite USY is sold commercially as Octacat cracking catalyst. This reaction is affected at temperatures ranging from ambient to 350° C., preferably from 100°-250° C. and most preferably from 180°-240° C. over a period required to produce desired conversion of reactants to product. Optionally, the reaction can be performed in a batch or semi-batch mode by continuous or partial addition of the catalyst or hydrocarbyl group to the thiophene. Catalyst can be used at levels ranging from 1 gram/mole of aromatic to 50 grams/mole of aromatic, preferably 5 grams/mole of aromatic to 50 grams/mole of aromatic, and most preferably from 10-30 grams/-mole of aromatic or more broadly 5 to 100 grams of catalyst to 1 mole of thiophene.

In general, the production of alkyled thiophenes is favored by the use of zeolite catalysts such as zeolite beta or zeolite Y preferably USY, of controlled acidity, preferably with an alpha value below about 200 and, for best results, below 100, e.g., about 25-50.

The above preferred method demonstrates the use of the catalysts of choice. MCM-22 is disclosed in U.S. Pat. No. 4,954,325 which is incorporatd herein in its entirety by reference. It is also described in U.S. Pat. No. 5,100,534, which is incorporated herein in its entirety by reference, as a crystalline aluminosilicate zeolite. MCM-22 is also described in U.S. Pat. No. 5,103,066 as having a CI (constraint index) of 1.5 at 454 C. U.S. Pat. No. 5,103,066 is incorporated herein by reference.

Constraint Index (CI) values for some typical zeolites are given below.

|  | CI (at test temperature) |
| --- | --- |
| ZSM-5 | 6-8.3 (371° C.–316° C.) |
| ZSM-22 | 7.3 (427° C.) |
| MCM-22 | 1.5 (454° C.) |
| Dealuminized Y | 0.5 (510° C.) |

The method by which Constraint Index of acidic zeolites is determined is described fully in U.S. Pat. No. 4,016,218 incorporated herein by reference for details of the method. The above-described CI is a highly important definition of the zeolites which are useful in the process of the present invention.

The alpha value of the zeolite is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 sec $-1$). The alpha test is described in U.S. Pat. No. 3,354,078 and In J. Catalysis, 4, 527 (1965); 6, 278 (1966); and 61, 395 (1980), to which reference is made for a description of the test. The experimental conditions of the test used to determine the alpha values referred to in this specification include a constant temperature of 538° C. and a variable flow rate as described in detail in J. Catalysis, 61, 395 (1980).

FCC (fluid catalytic cracking) catalysts based on ultrastable Y type (USY) zeolites are well known in the art to make gasoline having a higher octane number than FCC catalysts based on rare earth exchanged Y (REY) or calcined rare earth exchanged Y (CREY); see U.S. Pat. No. 5,102,530 which is incorporated herein by reference. It is further disclosed in U.S. publication/notice H 449 (Mar. 1, 1988) to Rudesill that the commercially available FCC cracking catalyst (Octacat) comprises about 40% Ultrastable Type Y zeolite combined with a silica-alumina sol binder and kaolin matrix and that preferably the USY containing Octacat may comprise from about 15 to about 60 wt % USY and more preferably from about 35 to about 45 wt % USY. H 449, filed Jul. 3, 1987 and published Mar. 1, 1988 to Rudesill is incoporated herein by reference.

The alkylated thiophenes produced by this process may be represented generally by the structure:

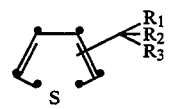

Where $R_1$, $R_2$ or $R_3$ may be H, alkyl, alkenyl, alkynyl, aryl, alkylaryl, cyclic, linear or branched as previously described;

and/or where $R_1$, $R_2$ or $R_3$ can contain S, N, O, P and/or F;

and/or where $R_1$, $R_2$ or $R_3$ are linked to form a cyclic structure.

The hydrocarbon compositions of the present invention relate to improved thermally and oxidatively stable fluids. These may be used optionally as liquid lubricants or in liquid lubricant compositions, and as solid lubricants or in solid lubricant compositions including greases, such as polyurea, lithium carboxylate or clay-thickened greases.

These hydrocarbon compositions may also be used in combination with additives, for example, antioxidants, EP/antiwear agents, inhibitors, detergents and dispersants, and viscosity index improvers. Non-limiting examples of antioxidants include phenols which can be hindered and aromatic amines.

Non-limiting examples of EP/antiwear additives include zinc phosphorodithioates, sulfurized esters, sulfurized olefins, phosphonates, phosphates, phosphordithionates, etc. Non-limiting examples of inhibitors include DMTD, phenothiazine, etc. Non-limiting examples of detergents and dispersants include sulfonates, phenates and polymeric succinimides. These can be either metallic or non-metallic. Metallic detergents can be calcium or magnesium derived and can be neutral or over based.

The hydrocarbon compositions of this invention can be used alone or in combination with other synthetic and/or mineral oil fluids.

Fuel compositions are also contemplated for use herein, these include both hydrocarbon fuels, including gasoline, naphtha and diesel fuels or alcoholic fuels or mixtures of alcoholic and hydrocarbon fuels. Fuel compositions can contain 10 to 1000 pounds of additive per 1000 barrels of fuel or more preferably 25 to 250 pounds per 1000 barrels of fuel.

When the compositions of the present invention are used alone or in combination with other synthetic and/or mineral oil fluids, the below described oils of lubricating viscosity may be used. When used as the basestock or feedstock the alkylated thiophenes of the present invention will generally have a viscosity range varying from about 3 to about 20 cSt at 100° C. with a preferred range of 3.5-10.

The fluids in accordance with the invention have been found to be highly useful when combined or blended with synthetic or mineral based fluids and particularly with ester-containing fluids such as synthetic polyalpholefins (PAO). Any suitable blending ratio may be used, for example, a blend of 20% alkylated thiophenes and 80% PAO has been found to be very advantageous. However, the alkylated thiophenes may constitute a majority of the blends up to about 80–100% or less than 100%. It is noted that alkylated thiophene fluids may be used as replacements for or as components of current commercial lubricant formulations.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. and preferably, from about 50 to about 250 SSU at 210° F. These oils may have viscosity indexes ranging to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for foaming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether and phenoxy phenylethers.

EXAMPLES

The following examples are exemplary only and are not intended to limit the invention.

EXAMPLE 1

To a vigorously stirred mixture of thiophene (84.14 g, 1.0 mole) and 1-tetradecene (196 g, 1.0 mole) in a flask fitted with thermocouple and reflux condenser was added 15 g of FCC Octacat USY catalyst. The mixture was heated to 200° C. with stirring for six hours. After cooling to room temperature, the mixture was filtered to remove catalyst and vacuum distilled to 170° C. at 0.5–1.5 mmHg to remove unreacted starting materials.

EXAMPLE 2

Using the procedure in Example 1, thiophene (84.14 g, 1.0 mole) and 1-tetradecene (196 g, 1.0 mole) were reacted using 30 grams of FCC Octacat USY catalyst.

EXAMPLE 3

Using the procedure in Example 1, thiophene (84.14. g, 1.0 mole) and 1-dodecene (168.32 g, 1.1 moles) were reacted using 15 grams of FCC Octacat USY catalyst.

EXAMPLE 4

Using the procedure in Example 1, thiophene (84.14 g, 1.0 mole) and 1-hexadecene (224 g, 1.0 mole) were reacted using 15 grams of FCC Octacat USY catalyst.

EXAMPLE 5

Using the procedure in Example 1, thiophene (84.14 g, 1.0 mole) and 1-octadecene (252.5 g, 1.0 mole) were reacted using 15 grams of FCC Octacat USY catalyst.

EXAMPLE 6

To a stirred mixture of 1-octene (224.2 g, 2 moles), and thiophene, 84.14 g (1 mole), was added 2.0 grams of anhydrous AlCl3 and heated at reflux for six hours. The mixture was cooled, washed to remove inorganic materials, dried over anhydrous MgSO4. Gas chromatographic analysis showed essentially complete reaction of starting material. Color of this material was >5 whereas the product of Example 1 was <2.0.

EXAMPLE 7

Using the procedure in Example 6, 1-decene, 140.27 g (1 mole) and thiophene (84.14 g, 1 mole) were reacted with AlCl3 (2 grams) at reflux for six hours. Vacuum distillation of the washed organic mixture to 170° C. at 0.5–1.5 mmHg resulted in the desired hydrocarbyl thiophene product.

Typical properties of exemplary hydrocarbyl thiophene are shown in Table 1.

TABLE 1

| Hydrocarbyl | $C_{16}$ | $C_{16}$ |
|---|---|---|
| KV @ 100° C., cSt | 2.76 | 2.94 |
| VI | 129 | 132 |
| Pour Point (°F.) | −13 | −13 |

Performance Evaluation

In the Four-Ball Wear Test, three stationary balls are placed in a lubricant cup and a lubricant containing the compound to be tested is added thereto, and a fourth ball is placed in a chuck mounted on a device which can be used to spin the ball at known speeds and loads. The examples were tested using half inch stainless steel balls of 52100 steel for thirty minutes under 30 kg load at 1800 rpm and 200° F. If additional information is desired consult test method ASTM D226 and/or U.S. Pat. No. 4,761,482.

In the Four-Ball EP Test the weld load, in KG force, is determined by the ASTM D-2596 Four-Ball EP test in which a steel ball, under a constant force or load, is rotated at a speed of 1770 RPM against three other balls held in a stationary position in the form of a cradle. The temperature is maintained at 100° C. and the rotating ball is subjected to successively higher loads for 10 seconds until the four balls weld together. The results are summarized in Table 3 below.

K (as reported in Table 2) the wear coefficient is calculated from the wear volume, V, of the stationary ball. The wear volume is calculated from the wear scar diameter D in mm as follows:

$V = [15.5\ D^3 - 0.001033L]\ D \times 10^3$ mm3 where L is the machine load in kg. This equation considers the elastic deformation of the steel balls.

Wear Coefficient K

Dimensionless $K$ is defined as $K = \dfrac{VH}{dN}$ where V = wear volume, mm3
H = hardness 9725 kg/mm2 for 52100 steel
d = (23.3 mm/rev) (RPH × Time)
N = (0.408) (Load in kg)
f = the Coefficient of Friction
LNS = Last Non Seizure Load
LWI = Load Wear Index

TABLE 2

Four-Ball Wear Test Results
(200° F./40 Kg/30 min)

| | 1800 RPM | |
|---|---|---|
| | K factor ($\times\ 10^{-8}$) | f |
| $C_{16}$-thiophene | 8.8 | 0.088 |
| Commercial Synthetic Lubricant | 402 | 0.076 |

TABLE 3

Four-Ball EP (100° C.)

| | LNS | LWI | Weld |
|---|---|---|---|
| $C_{16}$-thiophene | 32 | 26.3 | 200 |
| Commercial Synthetic Lubricant | 32 | 14.6 | 126 |

The Four-Ball EP Test results demonstrate the excellent antiwear properties of these compositions.

PERFORMANCE AS A LUBRICANT WITH IMPROVED ADDITIVE SOLUBILITY

To a synthetic lubricant base stock was added 4.0 wt % of sulfurized isobutylene (as generally described by A. G. Horodysky in U.S. Pat. No. 3,703,504) and 0.5 wt % of a hindered phenolic inhibitor obtained from Ethyl Corp. as Ethyl 702. The mixture of additives was insoluble in the base stock and the sample was cloudy. To this mixture was added 21 wt % $C_{14}$ alkylated thiophene. The sample was mixed; the additives completely dissolved and the mixture became clear.

The use of alkylated thiophene as a suitable replacement for components of current lubricant formulations is highly desirable. For example, synthetic and/or mineral based lubricant compositions containing esters for improved additive solubility would be significantly improved by replacement with alkylated thiophene due to its excellent thermal stability, load-carrying properties and excellent additive solubility. Alkyl thiophenes prepared as described herein provide excellent base stock properties and could themselves serve as the base stock in formulations for various applications, for example, applications where high temperatures are maintained.

Although the present invention has been described with preferred embodiments, it is to be understood that modifications and variations may be resorted to, without departing from the spirit and scope of this invention, as those skilled in the art will readily understand. Such variations and modifications are considered within the purview and scope of the appended claims.

What is claimed is:

1. A process for the preparation of a high-temperature stable lubricant fluid or lubricant additive consisting of catalytically reacting in the presence of a fluid catalytic cracking zeolite catalyst (1) a hydrocarbyl moiety, having at least one olefinic group and optionally containing S, N, O, P, F, or mixtures thereof, and (2) a thiophene and wherein hydrocarbyl comprises cyclic, linear or branched containing from 3 to about 500 carbons wherein the reaction temperature varies from ambient to about 350° C., the molar ration of hydrocarbyl moiety to thiophene varies from 1:1 to about 10:1 and the amount of catalyst varies from 5 to about 100 grams of catalyst to about 1 mole of thiophene.

2. The process of claim 1 wherein the zeolite catalyst is selected from the group consisting of a zeolite X, a zeolite Y, UHP-Y, ZSM-12, ZSM-20, ZSM-22, FCC USY and MCM-22.

3. The process of claim 1 wherein the catalyst is FCC USY.

4. The process of claim 3 wherein the reactants are 1-tetradecene and thiophene and the catalyst is FCC USY.

5. The process of claim 3 wherein the reactants are 1-dodecene and thiophene and the catalyst is FCC USY.

6. The process of claim 3 wherein the reactants are 1-hexadecene and thiophene and the catalyst is FCC USY.

7. The process of claim 3 wherein the reactants are 1-octadecene and thiophene and the catalyst is FCC USY.

* * * * *